United States Patent [19]
Shelly

[11] Patent Number: 5,437,620
[45] Date of Patent: Aug. 1, 1995

[54] WRIST SPLINT

[75] Inventor: Randy L. Shelly, De Soto, Tex.

[73] Assignee: Bio Tex Ltd., Inc., Cedar Hill, Tex.

[21] Appl. No.: 21,998

[22] Filed: Feb. 24, 1993

[51] Int. Cl.$^6$ .............................................. A61F 5/10
[52] U.S. Cl. .............................. 602/21; 601/40; 602/12; 602/13; 602/22
[58] Field of Search ............... 602/12, 13, 21, 22; 128/26, DIG. 20; 601/40

[56] References Cited

U.S. PATENT DOCUMENTS

| | | | |
|---|---|---|---|
| 1,389,741 | 9/1921 | Cotton | 602/21 |
| 2,520,035 | 8/1950 | Goldberg | 602/21 |
| 2,863,449 | 12/1958 | Spencer | 602/21 |
| 3,581,740 | 6/1971 | Sherbourne | 602/21 X |
| 3,769,970 | 11/1973 | Swanson | 602/21 |
| 4,366,812 | 1/1983 | Nuzzo | 602/22 |
| 4,907,574 | 3/1990 | Hollerbach | 128/DIG. 20 |
| 4,977,890 | 12/1990 | Mann | 602/21 |
| 5,020,515 | 6/1991 | Mann et al. | 128/26 |
| 5,056,504 | 10/1991 | Mann | 602/21 X |

*Primary Examiner*—Steven A. Bratlie
*Attorney, Agent, or Firm*—Harris, Tucker & Hardin; George R. Schultz

[57] ABSTRACT

A wrist splint (10) is disclosed, comprising a splint platform (20), at least one bladder receptacle member (16, 18) slidingly engaged with the splint platform (20) and at least one air bladder (12, 14), each air bladder (12, 14) coupled to one of the bladder receptacle members (16, 18). Other devices, systems and methods are disclosed.

15 Claims, 2 Drawing Sheets

WRIST SPLINT

TECHNICAL FIELD OF THE INVENTION

The present invention relates to medical devices for limb positioning, and more particularly to a wrist splint for restoring a hand from a contracted position to a normal position.

BACKGROUND OF THE INVENTION

The elderly in general, and particularly patients who suffer from arthritis, are especially prone to a condition known as contracture. Contracture is the involuntary contraction of the muscles in the hand and wrist which cause the hand to rest in a closed, fist-like position, rather than in the slightly arched position of the normal relaxed hand. Contracture results from the shortening and thickening of the connective tissue which restricts the range of motion of the hand and wrist.

Contracture in an arthritic patient's hand may be corrected by the steady application of pressure having a tendency to force the patient's hand open and move it toward a normal relaxed position. Such pressure must be applied continuously over a period of time for the therapy to be successful. Additionally, the pressure must be periodically adjusted to account for movement of the patient's hand from the contracted position toward a normal position, so that the pressure is always tending to force the hand away from it's current position until a normal position is reached.

Prior art devices designed to correct contracture have suffered from many problems. A typical prior art device is illustrated in FIG. 1 and indicated generally at 100. The device 100 is shown in use by a patient and includes an air bladder 102 which may be inflated and deflated by means of valve 104. Air bladder 102 is coupled to wrist piece 106 which is secured to the patient's forearm by means of straps 108 and 110. Device 100 is used by inflating air bladder 102 with a first amount of air. This will cause air bladder 102 to apply pressure to the contracted hand, forcing the fingers away from the palm. After some period of time, the hand will adjust to this new position, and the air bladder 102 may then be further inflated with a second amount of air. This will cause air bladder 102 to apply further pressure to the hand, further forcing the fingers away from the palm. This procedure may be repeated as many times as necessary to slowly move the patient's fingers away from the palm.

An example of such prior art wrist splints to treat contracture is disclosed in U.S. Pat. No. 5,020,515 to Mann entitled "Inflatable Hand Splint". A similar device is disclosed in U.S. Pat. No. 5,056,504 also to Mann and also entitled "Inflatable Hand Splint". These prior art devices have the disadvantage that the fingers are moved away from the palm, but the hand is left in a semi-contracted position after treatment (i.e. the fingertips are still contracted). This is due to the fact that the distance the patient's fingers may be moved is limited by the thickness of air bladder 102 when fully inflated. Even a relatively large air bladder 102 will not be able to completely correct the contracture, because pressure is not applied to the patient's hand at the correct locations and in the correct directions to affect this. Furthermore, these prior art devices utilize a pliable wrist support element 106 which does not adequately support the patient's wrist during therapy. This pliable wrist support element is inadequate because it allows the patient's hand to bend at the wrist during therapy.

Consequently, there is a need for a device which will restore a patient's contracted hand to a normal, slightly arched, relaxed position while maintaining good support for the wrist. The present invention is directed toward meeting this need.

SUMMARY OF THE INVENTION

It is therefore the object of the present invention to provide a contracture correction device which overcomes most of the problems of the prior art devices, by providing a single device which can be used to apply pressure throughout the entire range of hand positions from fully contracted to fully normal. It is also an object of the present invention to provide a contracture correction device which is effective in correcting contracture effects in the first joint of the fingers.

In accordance with the present invention a wrist splint is disclosed, comprising a splint platform, at least one rigid bladder receptacle member slidingly engaged with the splint platform and at least one air bladder, each air bladder coupled to one of the bladder receptacle members.

In another form of the invention, a wrist splint for correcting contracture of a hand is disclosed, comprising a splint platform, a first rigid bladder receptacle member slidingly engaged with the splint platform, a first air bladder coupled to the first bladder receptacle member, a second rigid bladder receptacle member slidingly engaged with the splint platform and a second air bladder coupled to the second bladder receptacle member.

In another form of the invention, a method for correcting contracture of a hand of a patient is disclosed, comprising the steps of inserting an air bladder between a palm and fingers of the hand, increasing an inflation of the air bladder until pressure is exerted on the palm and the fingers, forcing the fingers toward a noncontracted position and moving the air bladder away from a wrist of the patient after a period of time and fixing the air bladder at a position where it exerts pressure on the fingers, forcing them toward a noncontracted position.

BRIEF DESCRIPTION OF THE DRAWINGS

The novel features believed to be characteristic of the invention are set forth in the appended claims. The invention itself, however, as well as other features and advantages thereof, will be best understood by reference to the detailed description which follows, read in conjunction with the accompanying drawings, wherein:

DETAILED DESCRIPTION OF THE DRAWINGS

The present invention is directed towards a wrist splint for restoring a hand from a contracted position to a normal position. The preferred embodiment of the present invention will best be understood by reference to FIGS. 2-5 of the drawings, wherein like numerals are used to designate like and corresponding parts of the various drawings.

Figure 1:
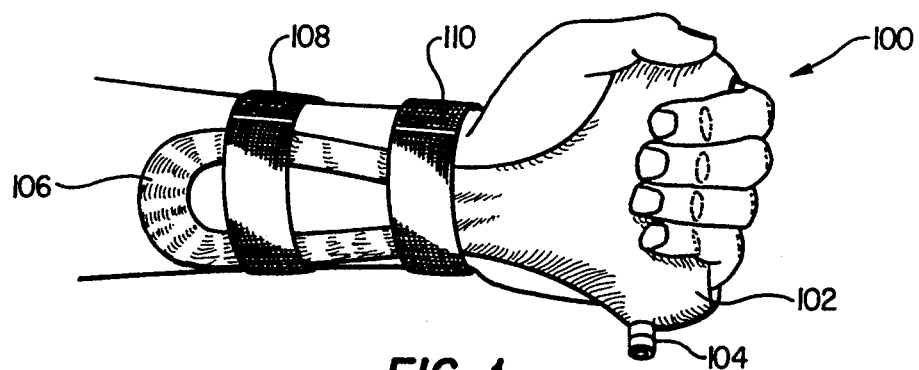
FIG. 1 is a bottom view of a prior art wrist splint in use on a patient's hand.
Figure 2:
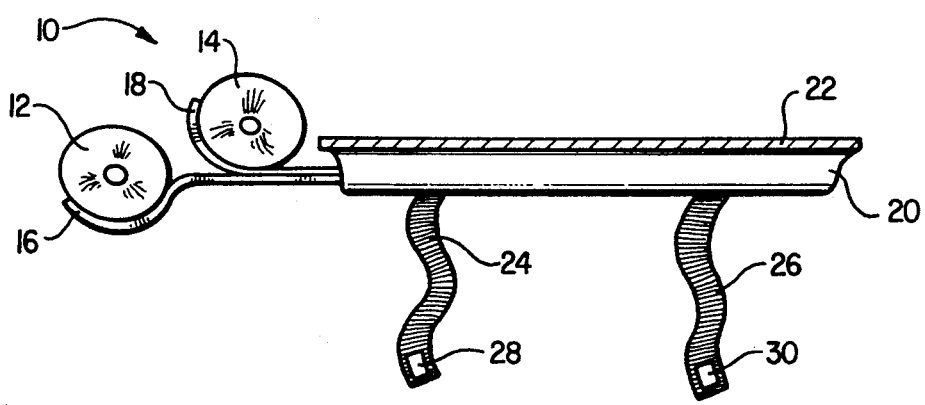
FIG. 2 is a side view of the wrist splint of the present invention.

Referring to FIG. 2, the wrist splint 10 of the present invention is shown. The wrist splint 10 includes a first air bladder 12 and a second air bladder 14. Air bladders 12, 14 are preferably constructed of PVC and filled with air to a pressure sufficient to maintain their desired size under light loading conditions. Air bladder 12 is fixedly attached to bladder receptacle member 16 and air bladder 14 is fixedly attached to bladder receptacle member 18 by any convenient means, such as epoxy for example. Bladder receptacle members 16, 18 are constructed of a rigid, nonpliable material such as ABS plastic or the like and are slidingly engaged with splint platform 20. Splint platform 20 is also constructed of a rigid, nonpliable material such as ABS plastic or the like. The upper surface of splint platform 20 is preferably covered with a relatively flexible material 22, such as material known by the trademark THERMOSTAT and manufactured by the DuPont Corporation, in order to provide a comfortable surface for the patient's arm. Splint platform 20 further includes straps 24 and 26 for securing the wrist splint 10 to the patient's arm. Straps 24 and 26 include fasteners 28 and 30, respectively, which may be hook and loop fasteners, for example.

Various covers (not shown) may be provided for portions of the wrist splint 10 for protection of the wrist splint 10, absorption of sweat to facilitate the patient's comfort, and also for sanitary purposes if the wrist splint 10 is to be used with more than one patient, such as in an institutional medical care facility. Separate covers may be provided which elastically surround each of the air bladders 12, 14. Also, a cover may be provided to encase splint platform 20. Such a cover may have, for example, a zipper, snap or hook and loop closure. Such covers may be, for example, constructed of material known by the trademark THERMOSTAT and manufactured by the DuPont Corporation. Such covers may be washed an reused many times.

Figure 3:
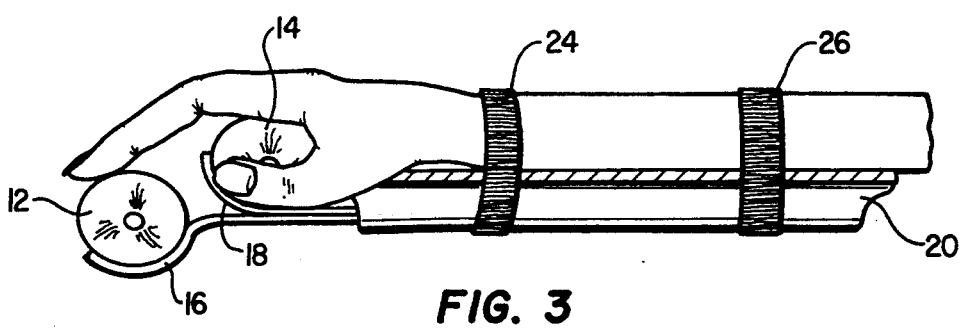
FIG. 3 is a side view of the wrist splint of the present invention in use on a patient's hand.

Referring now to FIG. 3, the wrist splint 10 is shown secured to a patient's arm. In order to correct contracture of an arthritic patient's hand, the wrist splint of the present invention is adjusted by sliding bladder receptacle members 16, 18 to a position which will cause the patient's hand to move slightly from its contracted position toward a normal position. For patients with severe contracture, air bladder 12 may have to be removed at this point in the therapy by sliding bladder receptacle member 16 fully from splint platform 20. This allows bladder receptacle member 18 to be positioned so that air bladder 14 alone causes the patient's hand to move slightly from a contracted position toward a normal position. When bladder receptacle members 16 and/or 18 are adjusted to their desired position, they are immobilized by means of a mounting bolt 64 (see FIG. 4d) and the wrist splint 10 is secured to the patient's wrist by means of straps 24, 26 and fasteners 28, 30. It is an important feature of the present invention that the rigid bladder receptacle members 16, 18 provide support for the patient's wrist during the entire therapy period, no matter what position they are adjusted to.

After pressure has been applied to the patient's hand for a period of time, the hand will adapt to the new, semi-contracted position. At this point, the wrist splint 10 will not be exerting any appreciable pressure against the patient's hand, because the hand now rests at its current position when relaxed. Therefore, at time intervals to be determined by the attending physician, the wrist splint 10 is further adjusted in order to continue to move the patient's hand from a contracted position toward a normal position. To do this, the mounting bolt 64 is loosened, and air bladders 12 and/or 14 are positioned by sliding bladder receptacle members 16 and/or 18 in order to move the patient's hand further from a contracted position toward a normal position. Once wrist splint 10 is adjusted to the desired position, mounting bolt 64 is tightened to fix the positioning of the various component pieces. This process may be repeated as many times and as often as the attending physician determines is necessary until the patient's hand has been returned to a normal, slightly arched position.

The ability of air bladder receptacles 16, 18 to slide in and out of splint platform 20, as well as the ability to adjust the size of the air bladders 12, 14, allows the wrist splint 10 to be used with a wide range of hand sizes. It further allows the wrist splint 10 to be used with hands exhibiting differing amounts of contracture, from full contracture to semi-contracted, returning them to a normal relaxed position. The flexibility and adjustability of the wrist splint 10 of the present invention allows the attending physician to customize a therapy regime for each individual patient.

Referring now to FIG. 4, the wrist splint 10 is shown disassembled into its various component parts. FIG. 4a illustrates air bladders 12, 14, which are substantially cylindrical in shape and wide enough to apply pressure across substantially the entire width of the patient's hand during treatment. Air bladders 12, 14 include valve 40 which is operable to admit or release air into or out of the air bladder so that wrist splint 10 may be adjusted to fit the size of the patient's hand. Air may be added to air bladders 12, 14 by means of a suitable pump device (not shown) which will attach to valve 40 and inflate the air bladders. Air bladders 12, 14 are described as being filled with air, but the present invention comprehends air bladders which are filled with any gas or liquid substance which would allow for their size to be adjusted.

Figure 4A:
FIG. 4a–e are perspective views of the component parts of the wrist splint of the present invention.
Figure 4B:
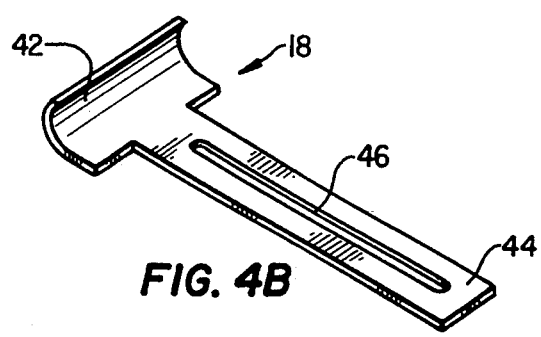

FIG. 4b illustrates bladder receptacle member 18, including bladder mounting surface 42, sliding member 44 and slot 46. Bladder mounting surface 42 is formed to extend outward and arch upward from sliding member 44, and has a width substantially equal to the width of air bladder 14. The upward arch of bladder mounting surface 42 causes air bladder 14 to be sandwiched between bladder receptacle member 18 and the palm of the patient's hand (as shown in FIG. 3), substantially eliminating any shear stress applied by the patient's hand to the epoxy attaching air bladder 14 to bladder receptacle member 18. Sliding member 44 engages with splint platform 20 and has sufficient width and thickness to provide adequate torsional stability to the assembled wrist splint 10. Slot 46 is provided to secure bladder receptacle member 18 after positioning as described hereinafter. Bladder receptacle member 18 is constructed of a rigid material, such as ABS plastic or the like, in order to support the patient's wrist during the course of therapy.

Figure 4C:
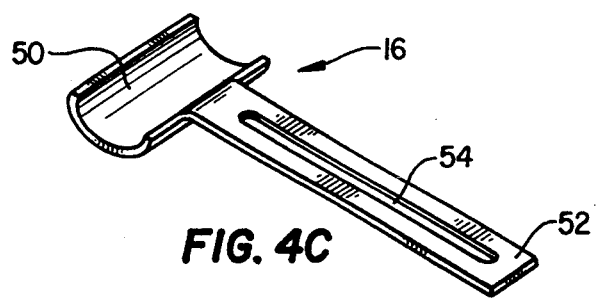

FIG. 4c illustrates bladder receptacle member 16, including bladder mounting surface 50, sliding member 52 and slot 54. Bladder mounting surface 50 is formed in an arched configuration which extends below sliding member 52, and has a width substantially equal to the width of air bladder 12. The downward arch of bladder mounting surface 50 causes air bladder 12 to be sandwiched between the patient's fingertips and bladder receptacle member 16 (as shown in FIG. 3), substantially eliminating any shear stress applied by the patient's hand to the epoxy attaching air bladder 12 to bladder receptacle member 16. Sliding member 52 engages with splint platform 20 and has sufficient width and thickness to provide adequate torsional stability to the assembled wrist splint 10. Slot 54 is provided to secure bladder receptacle member 16 after positioning as described hereinafter. Bladder receptacle member 16 is also constructed of a rigid material, such as ABS plastic or the like, in order to further support the patient's wrist during the course of therapy.

Figure 4D:
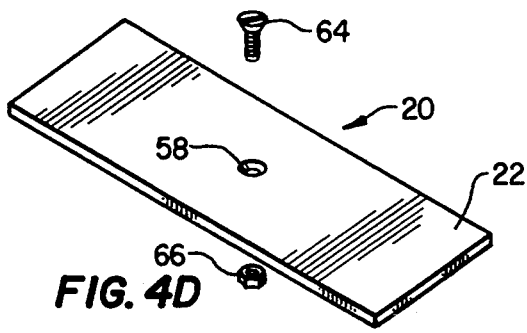

FIG. 4d illustrates a top perspective of splint platform 20, including flexible material 22 and mounting bolt hole 58. Mounting bolt hole 58 extends through the entire thickness of splint platform 20. When bladder receptacle members 16, 18 have been engaged in splint platform 20 and adjusted to their desired positions, a mounting bolt 64 is inserted into mounting bolt hole 58, through slots 46 and 54 and out the bottom of splint platform 20. A nut 66 is fastened to the end of the mounting bolt 64 and tightened, thereby securing the bladder receptacle members 16, 18 into place at their desired locations. The slots 46, 54 allow for infinite adjustability of the positions of bladder receptacle members 16, 18 throughout their range of motion. Because of the rigid construction of splint platform 20 and bladder receptacle members 16, 18, as well as their secure interconnection, the assembled wrist splint 10 provides adequate support for the patient's wrist throughout the therapy period.

Figure 4E:
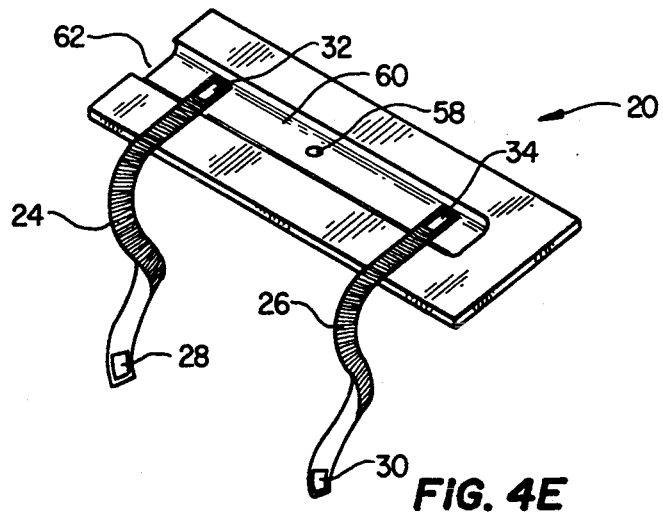

FIG. 4e illustrates a bottom perspective of splint platform 20, including straps 24, 26, fasteners 28, 30, 32, 34, mounting hole 58, cavity 60 and cavity opening 62. Fasteners 32 and 34 are provided for mating with fasteners 28 and 30, respectively. Fasteners 28, 30, 32 and 34 may be hook and loop fasteners, for example. Cavity 60 is formed with cavity opening 62 for sliding engagement of bladder receptacle members 16, 18. The dimensions of cavity 62 and cavity opening 62 are selected to provide a snug fit when both bladder receptacle members 16, 18 are engaged, thereby minimizing the strain against the tightened mounting bolt 64.

Figure 5:
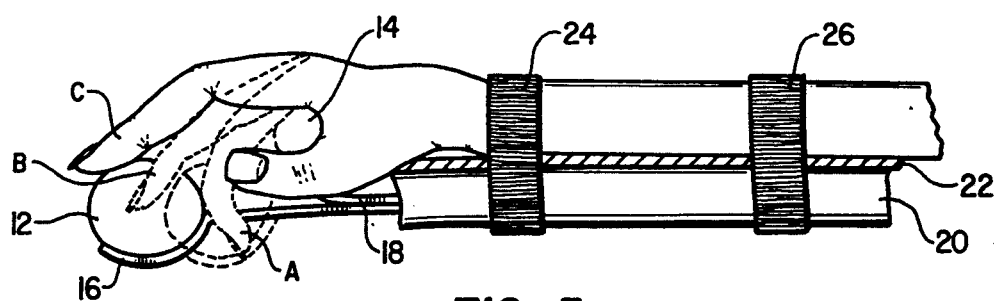
FIG. 5 is a side view of the wrist splint of the present invention in various positions during the course of treatment.

Referring now to FIG. 5, the wrist splint 10 is shown in various stages of operation during the course of a typical patient's therapy. The patient's hand begins at position A, where it is exhibiting contracture. At this point in the therapy, air bladder 12 is not used, and air bladder 14 is positioned as shown by adjustment of bladder receptacle member 18. If the patient's hand is fully contracted (i.e. the fingers are against or nearly against the palm), it may be necessary to deflate air bladder 14, slide air bladder 14 and bladder receptacle member 18 between the patient's fingers and palm, and then slightly inflate air bladder 14 in order to apply pressure to lift the fingers away from the palm. The first several stages of therapy may consist of progressively increasing the amount of air in air bladder 14 (therefore increasing its size) in order to move the patient's fingers far enough away from the palm so that they may then be pushed toward a fully open position. At the hand position shown in position A, air bladder 14 applies pressure at the base of the patient's fingers, forcing the hand away from its contracted position. No pressure is applied to the fingertips at this point.

At position B, air bladder 14 is not visible, but it has been moved further to the left of its location at position A by sliding bladder receptacle member 18 further out of splint platform 20. This allows air bladder 14 to apply pressure to the base of the patient's fingers, forcing them away from a contracted position and toward a normal position. Additionally, air bladder 12 has now been added to the wrist splint 10 and bladder receptacle member 16 is positioned so that air bladder 12 applies pressure to the patient's fingertips as they rest upon it, thereby contributing to the movement of the patient's hand from a contracted position to a normal position. At position B, the patient's hand has improved and now exhibits only slight contracture.

At position C, both the air bladder 14 (not visible) and the air bladder 12 have been moved further to the left of their respective locations at position B in order to continue to apply pressure to the patient's hand as it adjusts to its new position. Air bladders 12, 14 are positioned by sliding respective bladder receptacle members 16, 18 further out of splint platform 20. At position C, the patient's hand is now at a normal, relaxed position, and the previous contracture has been corrected. Of course, many intermediate positions of the wrist splint 10 may be required during the course of therapy, and positions A, B and C are shown only to illustrate the progressive recovery of the patient's hand during the course of therapy. It will be appreciated that the wrist splint 10 provides rigid support for the patient's wrist throughout the entire range of adjustment during therapy.

The wrist splint 10 of the present invention solves most the problems of the prior art devices. The single wrist splint 10 provides pressure therapy throughout the entire range of hand positions from full contracture to normal. This is made possible by the use of two adjustable air bladders which may be inflated or deflated and positioned relative to the patient's wrist over a wide range. The present invention further provides correction of contracture of the patient's fingertips by allowing the air bladders to be extended so as to apply pressure at the ends of the patient's fingers. Finally, the present invention provides rigid support for the patient's wrist throughout the course of therapy.

Although preferred embodiments of the invention have been described in the foregoing Detailed Description and illustrated in the accompanying drawings, it will be understood that the invention is not limited to the embodiments disclosed, but is capable of numerous rearrangements, modifications and substitutions of parts and elements without departing from the spirit of the invention. Accordingly, the present invention is intended to encompass such rearrangements, modifications and substitutions of parts and elements as fall within the scope of the invention.

What is claimed is:

1. A wrist splint for correcting contracture of a hand, comprising:
    a splint platform;
    at least one rigid bladder receptacle member slidingly engaged with said splint platform; and
    at least one air bladder, each said air bladder coupled to one of said at least one rigid bladder receptacle member.

2. The wrist splint of claim 1, wherein each said air bladder includes a valve which is operable to allow each said air bladder to be inflated or deflated, thereby changing its size.

3. The wrist splint of claim 1, further including means for securing said at least one rigid bladder receptacle member so that said at least one rigid bladder receptacle member remain stationary with respect to said splint platform.

4. A wrist splint for correcting contracture of a hand, comprising:
   a splint platform;
   a first rigid bladder receptacle member slidingly engaged with said splint platform;
   a first air bladder coupled to said first bladder receptacle member;
   a second rigid bladder receptacle member slidingly engaged with said splint platform; and
   a second air bladder coupled to said second bladder receptacle member.

5. The wrist splint of claim 4, wherein said first and second air bladders each include a valve which is operable to allow each said air bladder to be inflated or deflated, thereby changing its size.

6. The wrist splint of claim 4, wherein said first and second bladder receptacle members may be moved independently of each other.

7. The wrist splint of claim 4, further including means for securing said first and second bladder receptacle members so that they remain stationary with respect to said splint platform.

8. The wrist splint of claim 4, further including at least one strap for attachment of said splint platform to a patient.

9. A method for correcting contracture of a hand of a patient, comprising the steps of:
   inserting an air bladder between a palm and fingers of said hand;
   increasing an inflation of said air bladder until pressure is exerted on said palm and said fingers, forcing said fingers toward a noncontracted position; and
   moving said air bladder toward said fingers and away from a wrist of said patient after a period of time and fixing said air bladder at a position where it exerts pressure on said fingers, forcing them toward a noncontracted position.

10. The method of claim 9, further including the step of fixing a second air bladder at a second position where it exerts pressure on tips of said fingers, forcing said fingers toward a noncontracted position.

11. A wrist splint for correcting contracture of a hand, comprising:
   a splint platform for attachment to an underside of a patient's forearm;
   a first rigid bladder receptacle member slidingly engaged with said splint platform;
   a first air bladder coupled to said first bladder receptacle member;
   a second rigid bladder receptacle member slidingly engaged with said splint platform; and
   a second air bladder coupled to said second bladder receptacle member,
   wherein said first air bladder is positioned adjacent a palmer region of said hand and said second air bladder is positioned adjacent an underside of said patient's fingers, such that gradual removal of said first and second rigid bladder receptacle members from said splint platform forces said hand from a contracted position.

12. The wrist splint of claim 11, wherein said first and second air bladders each include a valve which is operable to allow each said air bladder to be inflated or deflated, thereby changing its size.

13. The wrist splint of claim 11, wherein said first and second bladder receptacle members may be moved independently of each other.

14. The wrist splint of claim 11, further including means for securing said first and second bladder receptacle members so that they remain stationary with respect to said splint platform.

15. The wrist splint of claim 11, further including at least one strap for attachment of said splint platform to a patient.

* * * * *